(12) United States Patent
Ma (10) Patent No.: US 6,205,238 B1
(45) Date of Patent: Mar. 20, 2001

(54) APPARATUS AND METHOD FOR INSPECTING LEADS OF AN IC

(75) Inventor: Yeon Soo Ma, Suwon (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/143,650

(22) Filed: Aug. 31, 1998

(30) Foreign Application Priority Data

Aug. 30, 1997 (KR) .................................................. 97-44867

(51) Int. Cl.[7] .............................. G06K 9/36; G06K 9/82
(52) U.S. Cl. ........................................ 382/146; 250/559.34
(58) Field of Search ............................ 382/103, 145–151, 382/154, 318; 348/87, 126, 94, 95; 250/559.34; 702/40, 94, 95, 150; 356/375, 376, 237.4, 237.5

(56) References Cited

U.S. PATENT DOCUMENTS

| | | | |
|---|---|---|---|
| 4,736,108 | * | 4/1988 | Comstock et al. ................... 250/561 |
| 4,739,175 | * | 4/1988 | Tamura ............................... 250/561 |
| 5,125,036 | * | 6/1992 | Raghavan et al. ...................... 382/8 |
| 5,134,665 | * | 7/1992 | Jyoko .................................... 382/8 |
| 5,162,866 | * | 11/1992 | Tomiya et al. ...................... 356/237 |
| 5,347,363 | * | 9/1994 | Yamanaka ........................... 356/376 |
| 5,406,372 | * | 4/1995 | Vodanovic et al. .................. 356/394 |
| 5,621,218 | * | 4/1997 | Tanaka ............................ 350/559.34 |

* cited by examiner

*Primary Examiner*—Leo Boudreau
*Assistant Examiner*—Brian P. Werner
(74) *Attorney, Agent, or Firm*—Burns, Doane, Swecker & Mathis, L.L.P.

(57) ABSTRACT

Disclosed are apparatus and method for inspecting leads of an IC placed on a setting table. The apparatus comprises an optical image recognition part for scanning the setting table, a device for moving the recognition palt with respect to the setting table, a position detection palt for detecting a position of the recognition part on the basis of an output signal thereof, and a control part for controlling the device on the basis of a signal of the position detection pait so that the recognition part is positioned at an optimal position above the setting table. The setting table is scanned stepwise, and the optimal position is a position that the value of the output signal is maximized. The recognition pall is positioned at the optimal position. The arrangement and the status of the leads of the IC are inspected automatically in a short period of time, and productivity increases.

9 Claims, 6 Drawing Sheets

APPARATUS AND METHOD FOR INSPECTING LEADS OF AN IC

BACKGROUND OF THE INVENTION

1. Field of the Invention

The present invention relates to an apparatus and a method for inspecting leads of an IC, and more particularly, to an apparatus and a method for precisely and automatically inspecting leads of an IC.

2. Description of the Prior Art

When the intervals between the leads of an IC and arrangement thereof are not even, the leads may get loose from a setting table while they are welded, which may cause a defect in electrical connection thereof. Thus, ICs have to be inspected before being installed on a PCB, and therefore, a variety of methods for inspecting the status of leads of an IC have been proposed.

Figure 6:
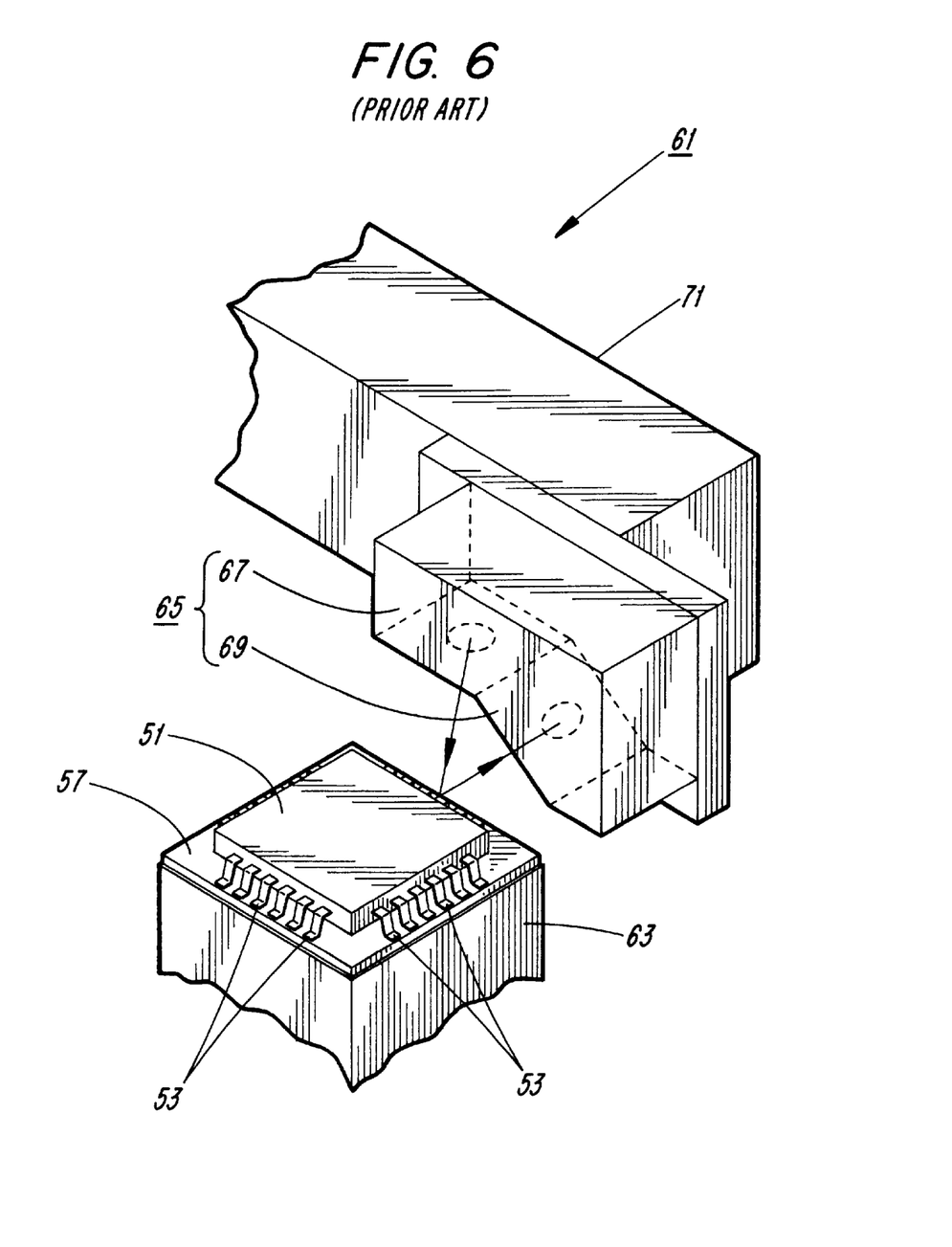
FIG. 6 is a partial perspective view of a conventional apparatus for inspecting leads of an IC.

FIG. 6 is a schematic partial perspective view of an apparatus for inspecting leads of an IC disclosed in U.S. Pat. No. 5,162,866. As shown in the figure, the conventional apparatus 61 for inspecting leads of an IC complises a setting table 57 on which ICs 51 are placed, a supporting part 63 for supporting the setting table 57, an optical image recognition part 65 disposed above the supporting part 63, and an image processor (not shown) for implementing the image of an inspection area on the basis of the output signals of the optical image recognition part 65.

The optical image recognition part 65 inspects the status of leads 53 of the IC 51 placed on the setting table 57. The optical image recognition part 65 has a laser beam source 67 and an optical sensing element 69. The laser beam source 67 projects a scan beam toward the IC 51 on the setting table 57, and the optical sensing element 69 receives the light reflected from the leads 53 of the IC 51. The optical image recognition part 65 is fixed to an arm 71, and the arm 71 can be moved horizontally and vertically by a driving device which is not shown.

In the conventional inspecting apparatus 61 having such a construction, when the setting table 57 on which the IC 51 is placed is supported by the supporting part 63, the optical image recognition part 65 is disposed above the setting table 57 by a manual operation of an operator or by a program stored in a control part. Then, the operator observes the image of the IC 51 implemented on the image processor while moving the optical image recognition part 65 with respect to the setting, table 57. When a position at which an optimal image can be achieved is detected during the observation, the operator disposed the optical image recognition part 65 on that position. In order to inspect precisely the intervals and arrangement of the leads 53, it is most important to dispose the optical image recognition part 65 at an optimal position.

Meanwhile, when the optical image recognition part 65 is disposed at the optimal position, the control part (not shown) moves the optical image recognition part 65 along a predetermined scan line. The laser beam source 67 projects the scan beam toward the leads 53 while the optical image recognition part 65 is moving, and the optical sensing element 69 receives the light reflected from the leads 53. The amount of reflected light received by the optical sensing element 69 valies according to the intervals and the arrangement of the leads 53, and the optical image recognition part 65 outputs pulses having the amplitude corresponding to the amount of the reflected light received by the optical image recognition part 65. The image processor implements the image of the leads 53 according to the output signal of the optical image recognition part 65, so the operator can determine the quality of the leads 53 of the IC 51.

Meanwhile, another type of apparatus for inspecting leads of an IC has been proposed which can detect the defect thereof automatically by comparing the output signals of the optical sensing element 69 with reference data about the quality of the leads of an IC.

Recently, the electrical appliances become small-sized and performance thereof becomes high, so the size of the IC 51 becomes smaller. Therefore, in order to inspect the intervals and arrangement of the leads 53 of an IC 51 with the conventional inspecting apparatus 61, the operator has to precisely control the distance between the IC 51 and the optical image recognition part 65 manually. Therefore, the inspection speed is low, and the preciseness of the inspection is lowered.

SUMMARY OF THE INVENTION

The present invention has been proposed to overcome the above-described problems of the conventional art. Therefore it is an object of the present invention to provide an apparatus and a method for inspecting leads of an IC, which can control the distance between the IC and an optical image recognition part automatically so that the intervals and the arrangement of the leads of the IC placed on a setting table can be inspected precisely and quickly.

To achieve the above object, the present invention provides an apparatus for inspecting leads of an IC placed on a setting table, said apparatus comprising: an optical image recognition part disposed above said setting table, said optical image recognition part for projecting a scan beam onto said setting table and receiving a light reflected therefrom; a driving means for moving said optical image recognition part with respect to said setting table; a position detection part for detecting a position of said optical image recognition part on the basis of an output signal of said optical image recognition part; and a control part for controlling said driving means on the basis of a detection signal of said position detection part so that said optical image recognition part is positioned at an optimal position above said setting table.

Preferably, said optical image recognition part comprises: a laser beam source for projecting the scan beam; and an optical sensing element for receiving the light reflected from said IC.

The image recognized by said optical image recognition part is implemented by an image processor.

According to the present invention, a method for inspecting leads of an IC placed on a setting table is provided, which comprises the steps of: preparing an optical image recognition part disposed above said setting table, said optical image recognition part being capable of moving with respective to said setting table, said optical image recognition part for projecting a scan beam onto said setting table and receiving a light reflected therefrom; scanning said setting table with said optical image recognition part while moving said optical image recognition part with respect to said setting table; determining an optimal position of said optical image recognition part on the basis of an output signal of said optical image recognition part during said step of scanning, said optimal position at which an optimal image of said IC can be achieved; and positioning said optical image recognition part at said optimal position.

It is preferable that said setting table is stepwise scanned.

Further, the step of determining said optimal position comprises the steps of: setting a temporary position of said optical image recognition part, said temporary position at which a value of said output signal is greater than a predetermined reference value; moving said optical image recognition pait from said temporary position in a direction which increases said value of said output signal; and detecting a position at which said value of said output signal is maximized.

Furthermore, said step of setting said temporary position comprises the steps of: positioning said optical image recognition part at a predetermined position; comparing said value of said output signal at said predetermined position with said reference value; regarding said predetermined position as said temporary position if said value of said output signal is greater than said reference value; moving said optical image recognition part if said value of said output signal is smaller than said reference value; and performing said step of comparing again after said step of moving.

Preferably, said optical image recognition part is moved up and down alternately from said predetermined position in said step of moving.

Moreover, the image of said IC is implemented during the step of scanning, according to said output signal of said optical image recognition part.

According to the present invention, the normality of the leads of the IC can be inspected automatically in a short period of time, and productivity increases.

BRIEF DESCRIPTION OF THE DRAWINGS

The above object and other advantages of the present invention will become more apparent by describing in detail the preferred embodiment of the present invention with reference to the attached drawings in which.

DESCRIPTION OF THE PREFERRED EMBODIMENT

Hereinbelow, the present invention will be described in detail with reference to the accompanying drawings. Parts identical to those in the conventional art will be referred to with the same reference numerals.

Figure 1:
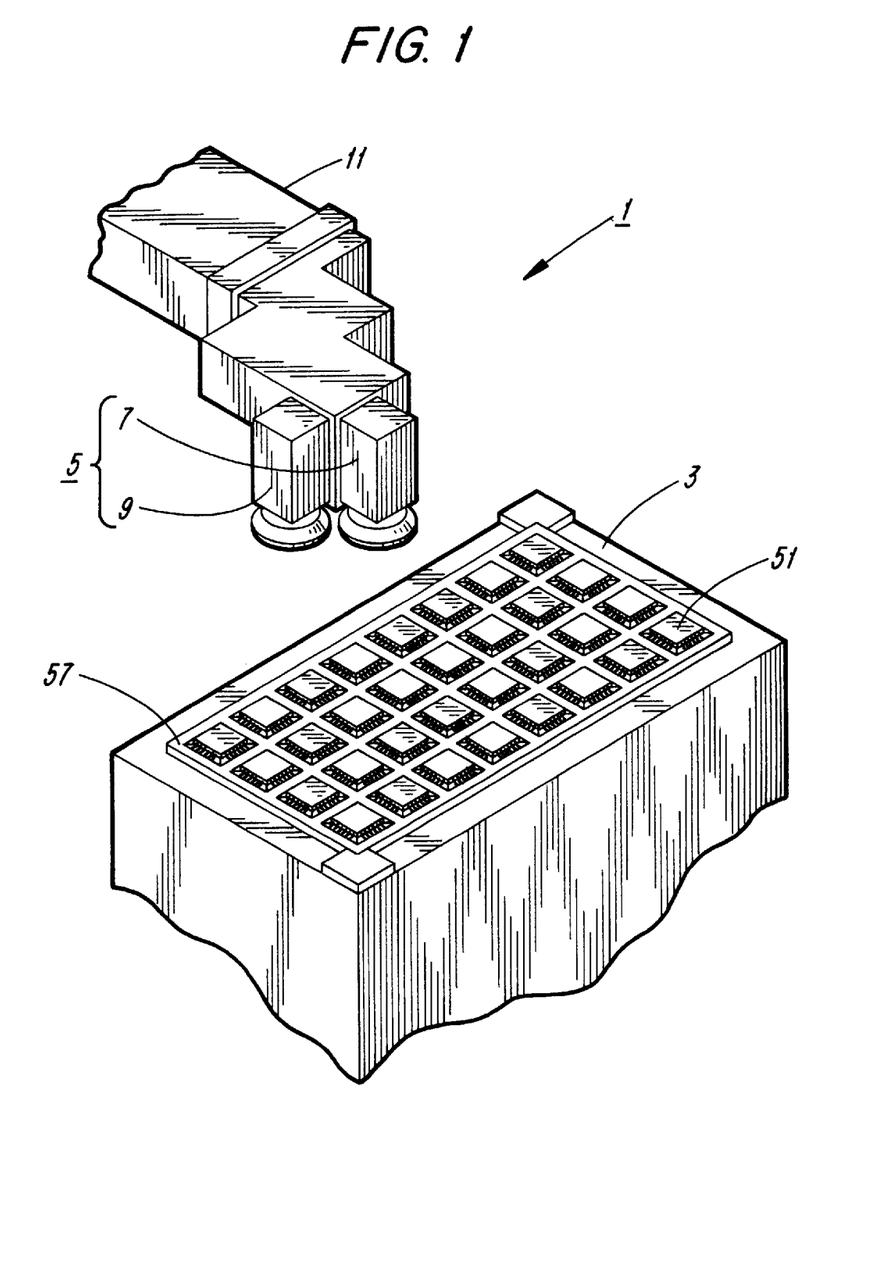
FIG. 1 is a partial perspective view of an apparatus for inspecting leads of an IC according to the present invention.

FIG. 1 is a partial perspective view of an apparatus for inspecting leads of an IC according to the present invention. The device for inspecting leads of an IC according to the present invention comprises, as the conventional device for inspecting leads of an IC which has been described with reference to FIG. 6, a setting table 57 on which ICs 51 are placed, a supporting part for supporting the setting table 57, an optical image recognition part 5 disposed above the supporting part 3, and an image processor (not shown) for implementing the image of the inspection area on the basis of the output signals of the optical image recognition part 5.

The optical image recognition part 5 inspects the status of leads 53 of the IC 51 placed on the setting table 57. The optical image recognition part 5 is fixed to an arm 11, and the arm 11 can be moved horizontally and vertically by a driving device which is not shown in the figure. The optical image recognition part 5 has a laser beam source 7 and an optical sensing element 9 tilted with respect to the laser beam source by a predetermined angle.

The laser beam source 7 projects a scan beam toward the ICs 51 on the setting table 57, and the optical sensing element 9 receives the light reflected from the leads 53 of the ICs 51. The optical sensing element can be simply constructed with a photosensitive diode.

Figure 2:
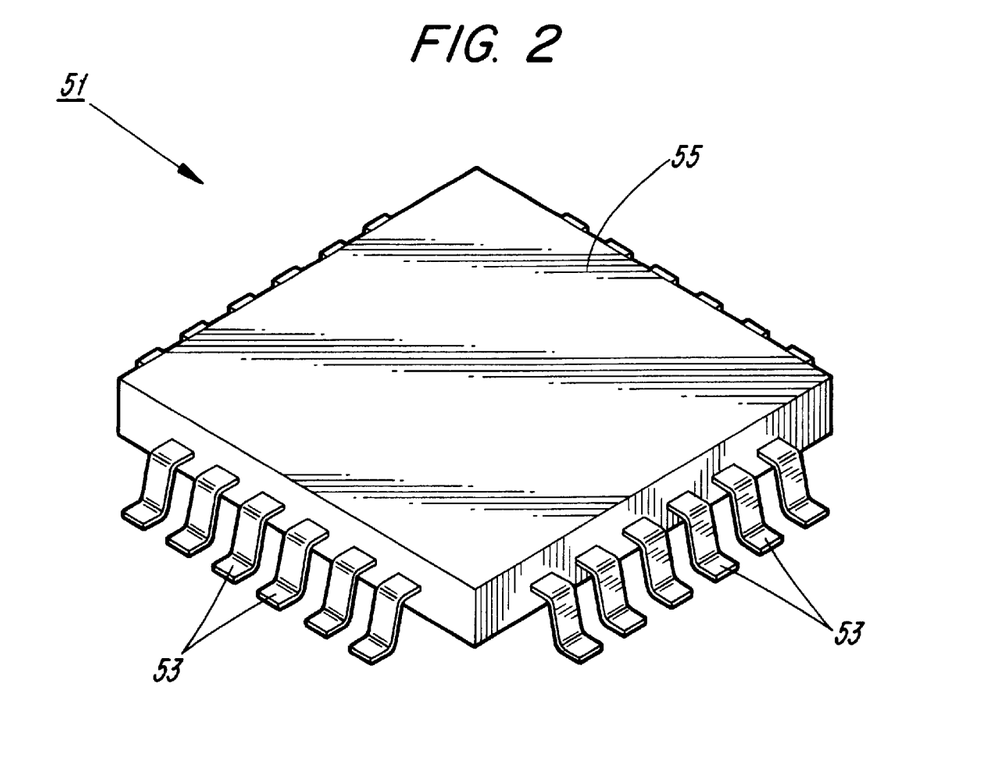
FIG. 2 is an enlarged perspective view of an IC.

Meanwhile, a plurality of ICs 51 forming a matrix are placed on the setting table 57. FIG. 2 is a perspective view of an IC. As shown in the figure, the IC 51 has a rectangular body 55 formed using a molding resin, and a plurality of leads 53 disposed along the edge of the body 55 by predetermined intervals.

Figure 3:
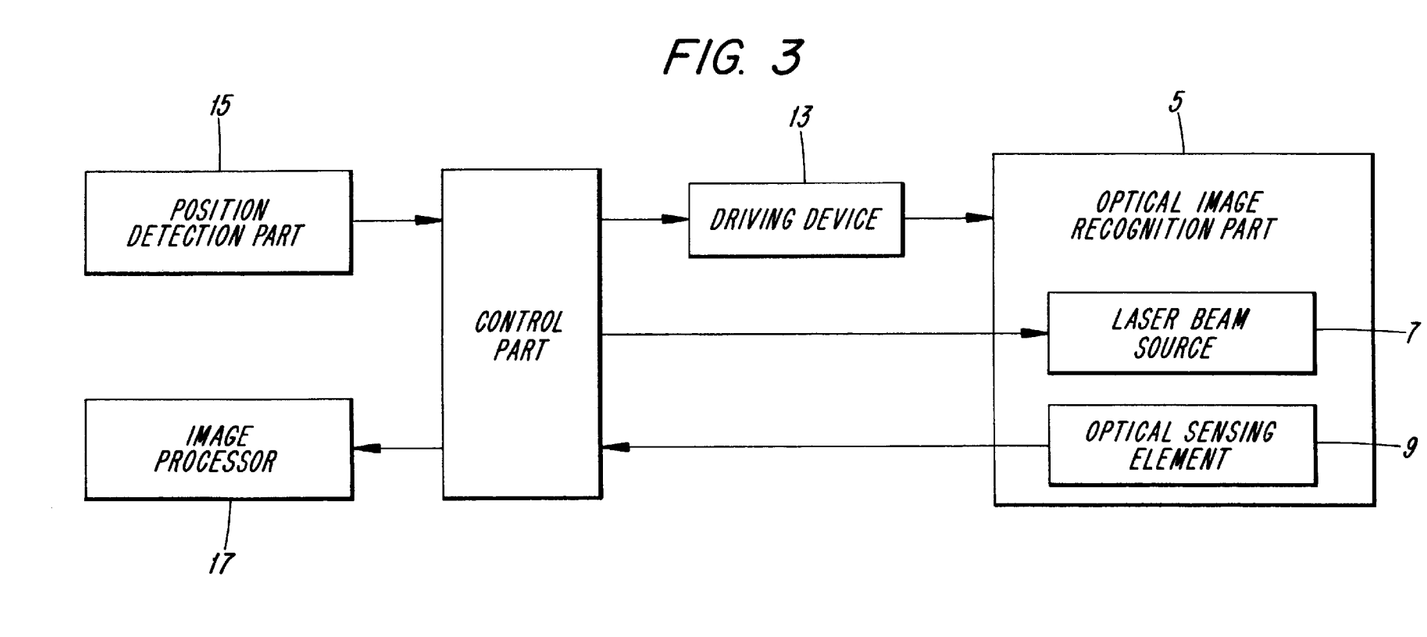
FIG. 3 is a block diagram of the apparatus for inspecting leads of an IC shown in FIG. 1.

Describing the device 1 for inspecting leads of an IC according to the present invention in more detail with reference to FIG. 3, the device 1 comprises an optical image recognition part 5 having a laser beam source 7 and an optical sensing element 9, a driving means 13 for moving the optical image recognition part 5 with respect to the setting table 57 vertically and horizontally, a position detection part 15 for detecting the position of the optical image recognition part 5 on the basis of the output signal of the optical image recognition part 5, and a control part 21 for controlling the driving device 13 on the basis of the detection signal from the position detection part 15 so that the optical image recognition part 5 is positioned at an optimal position above the setting table 57.

The position detection part 15 stores a reference amplitude TH corresponding to a signal pattern output when the optical image recognition part 5 is positioned at a position capable of scanning above the setting table 57. Thus, the position detection part 15 compares amplitude I(t) of the signal pattern at the present position of the optical image recognition part 5 with the predetermined reference amplitude TH, and then positions the optical image recognition part 5 at a position capable of scanning, that is, a temporary position which will be illustrated later. The control part 21 implements the image of the leads 53 of the IC 51 on the image processor 17 according to the detection signal of the position detection part 15.

Figure 4:
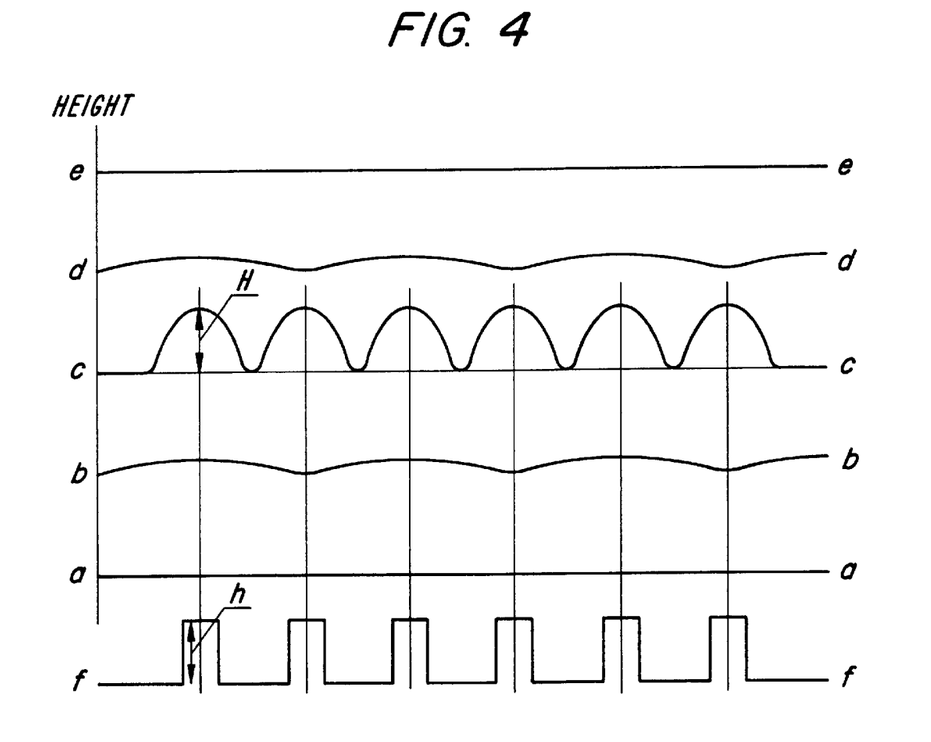
FIG. 4 is a graph showing a variety of signal patterns output from an optical image recognition part according to a distance between the optical image recognition part and a setting table.

Meanwhile, the signal patterns output from the optical image recognition part 5 respectively has amplitudes different from each other according to the distance from the setting table 57. FIG. 4 is a graph showing a variety of signal patterns output from the optical image recognition part 5 according to the distance between the optical image recognition pall 5 and the setting table 57. Positions a through e designate the height of the optical image recognition part 5. The graph f-f is an image pattern of the leads 53, and the amplitude h corresponds to the height of the lead 53. The graph c-c is a signal pattern output when the optical image recognition part 5 is positioned at an optimal position above the setting table 57. In that signal pattern, the amplitude H of the signal pattern corresponds to the height of the lead 53.

Meanwhile, if the optical image recognition part 5 is excessively close to or distant from the setting table 57, too much or too small amount of reflected light is received by the optical sensing element 9. Then, the optical image recognition part 5 outputs a linear signal pattern such as the graph a-a and e-e, so it is impossible to inspect the an arrangement of the leads 53. When the optical image recognition part 5 is positioned at the temporary position, the signal pattern like the graph b-b or d-d will be output. In the position detection part 15, the amplitude corresponding to the signal patterns b-b and d-d is stored as the reference amplitude TH.

Hereinbelow, the method for inspecting the leads of an IC according to the present invention having such a construction will be described.

Figure 5:
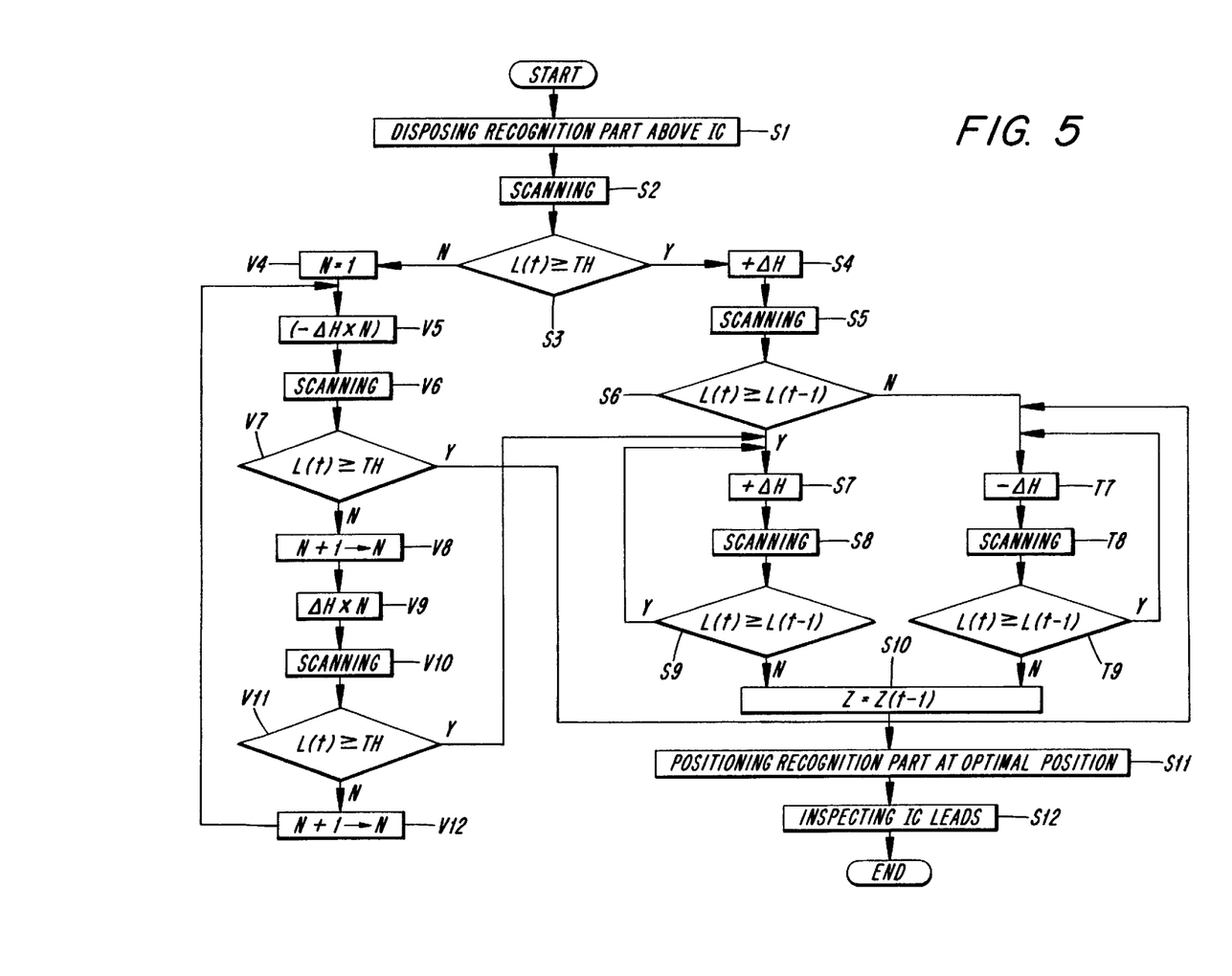
FIG. 5 is a flow chart for illustrating a method for inspecting leads of an IC according to the present invention.

FIG. 5 is a flow chart for illustrating the method for inspecting leads of an IC according to the present invention. The setting table 57 on which the ICs 51 are placed is supported on the supporting part 3. The control part 21 controls the control device 13 to dispose S1 the optical image recognition part 5 direct above the ICs 51. Then, the optical image recognition part 5 scans Hd the intervals and the arrangement of the leads 53 through the laser beam source 7 and the optical sensing element 9, and thereby a signal pattern corresponding thereto is output.

The position detection part 15 compares S3 the amplitude L(t) of the signal pattern output from the optical image recognition part 5 with the stored reference amplitude TH. In such a situation, if the amplitude L(t) of the output signal pattern is greater than the reference amplitude TH, the present position of the optical image recognition part 5 is regarded as the temporally position. The signal pattern output from the position detection part 15 at the temporary position will be the graph b-b or d-d, and an indistinct image will be implemented on the image processor 17.

In such a status, the optical image recognition part 5 is controlled so as to be positioned on an optimal position. At first, the optical image recognition part 5 is moved up S4 as much as a predetermined distance ΔH, and then the leads 53 are scanned S5. If the amplitude L(t) of the signal pattern output in such a status is greater than the amplitude L(t-1) at the previous position S6, the optical image recognition part 5 is moved up again S7 as much as a predetermined distance Δ H, and then the leads 53 are scanned S8. The movement and scanning are repeatedly performed until the amplitude L(t) of the output signal pattern becomes smaller than the amplitude L(t-1) at the previous step. When the amplitude L(t) of the output signal pattern becomes smaller than the amplitude L(t-1) at the previous step, the position at the previous step is determined S10 to the optimal position Z.

Meanwhile, if the amplitude L(t) of the output signal pattern is smaller than the amplitude L(t-1) at the previous step, the optical image recognition part 5 is moved down T7 as much as the predetermined distance ΔH, and the leads 53 are scanned T8. The amplitude L(t) of the output signal pattern is compared T9 with the amplitude L(t-1) at the previous step, and if the amplitude L(t) of the output signal pattern becomes smaller than the amplitude L(t-1) at the previous step, the position at the previous step is determined S10 to the optimal position Z. If the amplitude L(t) of the output signal pattern is greatel than the amplitude L(t-1) at the previous step, the movement and the scanning are repeatedly performed to determine the optimal position Z.

Meanwhile, if the amplitude L(t) of the signal pattern output from the optical image recognition part 5 is smaller than the reference amplitude TH S3, the signal pattern output from the optical image recognition part 5 will be the graph a-a or e-e, any image will not be implemented on the image processor 17. In order to dispose the optical image recognition part 5 at the temporary position, at first, the position amendment number N of the optical image recognition part 5 is set V4 to one. Then, the optical image recognition part 5 is moved down V5 as much as the predetermined distance ΔH, and the ICs 51 on the setting table 57 are scanned V6. In such a situation, if the amplitude L(t) of the output signal pattern is greater than the reference amplitude TH V7, the present position of the optical image recognition part 5 is regarded as the temporary position.

Then, the optical image recognition part 5 is moved down again T7 as much as the predetermined distance ΔH, and the leads 53 are scanned TS. The amplitude L(t) of the output signal pattern is compared T9 with the amplitude L(t-1) at the previous step. If the amplitude L(t) of the output signal pattern is smaller than the amplitude L(t-1) at the previous step, the position at the previous step is determined S10 to the optimal position Z. Meanwhile, if the amplitude L(t) of the input signal pattern is greater than the amplitude L(t-1) at the previous step, the downward movement and the scanning are repeatedly performed until the amplitude L(t) of the input signal pattern becomes smaller than the amplitude L(t-1) at the previous step, in order to determine S10 the optimal position Z of the optical image recognition part 5.

Meanwhile, although the optimal image recognition part 5 is moved down as much as the predetermined distance ΔH, if the amplitude L(t) of the output signal pattern is smaller than the reference amplitude TH, the position amendment number N is increased V8. Then, the optical image recognition part 5 is moved up V9 as much as the predetermined distance ΔH multiplied by the position amendment number N, and ICs 51 are scanned V10. In such a situation, if the amplitude L(t) of the input signal pattern is greater than the reference amplitude TH V11, the present position of the optical image recognition part 5 is regarded as the temporary position, Then, the optical image recognition part 5 is moved up S7 as much as the predetermined distance ΔH again S7, and the ICs 51 are scanned S8. The amplitude L(t) of the output signal pattern is compared S9 with the amplitude L(t-1) of the input signal pattern at the previous step. If the amplitude L(t) of the output signal pattern is smaller than the amplitude L(t-1) at the previous step, the position at the previous step is determined S10 as the optimal position Z. Meanwhile, if the amplitude L(t) of the output signal pattern is greater than the amplitude L(t-1) at the previous step V11, the upward movement and the scanning are repeatedly performed until the amplitude L(t) of the output signal pattern becomes smaller than the amplitude L(t-1) at the previous step, in order to determine S10 the optimal position Z of the optical image recognition part 5.

Although the optical image recognition part 5 is moved up as the step V9, the amplitude L(t) of the output signal pattern may be still smaller V11 than the amplitude L(t-1) of the signal pattern at the previous step. If such a case occurs, the position amendment number N is increased again V12 and the optical image recognition part 5 is moved down V5 as much as the predetermined distance ΔH multiplied by the position amendment number N, and thereafter the ICs 51 are scanned V6. Then, the optimal position Z of the optical image recognition part 5 is determined 510 according to the above-described order.

Meanwhile, when the optimal position Z of the optical image recognition part 5 is determined S10, the control part 21 controls the driving device 13 according to the detection signal from the position detection palt 15 so as to move S11 the optical image recognition part 5 toward the optimal position Z. When the optical image recognition part 5 is positioned at the optimal position Z, the output signal pattern becomes the graph c-c having a maximal amplitude. In such a situation, as described in relation to FIG. 6, the control part 21 inspect S12 the intervals and arrangement of the leads 53 of the ICs 51 placed on the setting table 57 according to a predetermined program stored therein to determine whether they are normal or not. Furthermore, since the image of the leads 53 of the ICs 51 are implemented distinctly on the image processor 17, the operator can inspect the status thereof with his/her own visual sense.

As described above, according to the present invention, the normality of the leads of the ICs can be inspected automatically in a short period of time, and productivity increases.

Although the present invention has been described and illustrated in detail, it is clearly understood that the same is by way of illustration and example only and is not to be taken by way of limitation, wherein the spirit and scope of the present invention is limited only by the terms of the appended claims.

What is claimed is:

1. An apparatus for inspecting leads of an IC, said apparatus comprising:

a setting table on which IC's are placed;

an optical image recognition part disposed above said setting table, said optical image recognition part including a beam source for projecting a scan beam onto said setting table, and a single sensing element disposed adjacent to the beam source for receiving me light beam reflected from the setting table;

a driving means for moving said optical image recognition part with respect to said setting table for scanning a plurality of leads;

a position detection part for detecting a position of said optical image recognition part above the setting table on the basis of an output signal of said optical image recognition part;

a control part for controlling said driving means on the basis of a detection signal of said position detection part so that said optical image recognition part is positioned at an optimal position above said setting table, whereby the reflected light beam received by the sensing element during scanning provides an optimum signal pattern representing a shape of the leads when the optimal position is achieved; and a comparing part for comparing the optimum signal pattern with a reference value representing a normal shape of the leads.

2. The apparatus for inspecting leads of an IC as claimed in claim 1, wherein:

the beam source comprises a laser beam source for projecting the scan beam; and the sensing element comprises an optical sensing element for receiving the light reflected from said IC.

3. The apparatus for inspecting leads of an IC as claimed in claim 1, further comprising an image processor for displacement an image recognized by said optical image recognition part.

4. A method for inspecting leads of a plurality of ICs placed on a setting table, said method comprising the steps of:

A. placing the plurality of ICs on the setting table below an optical recognition part which includes a light beam source and a single sensing element for receiving a reflected light beam;

B. scanning the table by emitting a light beam from the light beam source toward the table and receiving the light beam with the sensing element after it reflects back toward the optical recognition part, and emitting a signal in accordance with the received light beam;

C. scanning a plurality of leads by producing relative movement between the table and the optical recognition part during step B;

D. determining, on the basis of the signals emitted during scanning, an optimal position of the optical recognition part above the table for producing an optimal IC image;

E. positioning the optical image recognition part at the optimal position;

F. repeating steps B and C for successively scanning the ICs on the table and providing an optimal signal pattern representing the shape of the leads; and G. comparing the optimum signal patterns with a reference value representing a normal shape of the leads.

5. The method for inspecting leads of an IC as claimed in claim 4, wherein said setting table is stepwise scanned during step B.

6. The method for inspecting leads of an IC as claimed in claim 5, wherein step D comprises the steps of:

setting a temporary position of said optical image recognition part at which a value of said output signal is greater than a predetermined reference value;

moving said optical image recognition part from said temporary position in a direction which increases said value of said output signal; and detecting a position at which said value of said output signal is maximized.

7. The method for inspecting leads of an IC as claimed in claim 6, wherein said step of setting said temporary position comprises the steps of:

positioning said optical image recognition part at a predetermined position;

comparing said value of said output signal at said predetermined position with said reference value;

determining said predetermined position as said temporary position if said value of said output signal is greater than said reference value;

moving said optical image recognition part if said value of said output signal is smaller than said reference value; and performing said step of comparing again after said step of moving.

8. The method for inspecting leads of an IC as claimed in claim 7, wherein said optical image recognition part is moved up or down from said predetermined position in said step of moving.

9. The method for inspecting leads of an IC as claimed in claim 4, further comprising a step of displaying an image of said IC according to said output signal of said optical image recognition part during the step of scanning.

* * * * *